(12) United States Patent
Hausmann et al.

(10) Patent No.: US 7,342,717 B1
(45) Date of Patent: Mar. 11, 2008

(54) WAVE FIELD MICROSCOPE WITH DETECTION POINT SPREAD FUNCTION

(75) Inventors: Michael Hausmann, Ludwigshafen (DE); Christoph Cremer, Heidelberg (DE); Joachim Bradl, Schriesheim (DE); Bernhard Schneider, Speyer (DE)

(73) Assignee: Ruprecht Karts Universitaet Heidelberg, Heidelberg (DE)

( * ) Notice: Subject to any disclaimer, the term of this patent is extended or adjusted under 35 U.S.C. 154(b) by 0 days.

(21) Appl. No.: 09/462,435

(22) PCT Filed: Jul. 9, 1998

(86) PCT No.: PCT/DE98/01908

§ 371 (c)(1),
(2), (4) Date: Jun. 19, 2000

(87) PCT Pub. No.: WO99/02974

PCT Pub. Date: Jan. 21, 1999

(30) Foreign Application Priority Data

Jul. 10, 1997 (DE) ................................ 197 29 512

(51) Int. Cl.
*G02B 21/00* (2006.01)
(52) U.S. Cl. ...................... 359/370; 359/371; 359/372; 359/368
(58) Field of Classification Search ................ 356/357, 356/359, 363, 349, 351, 360, 375; 435/6, 435/287.2; 536/23.1; 359/370, 371, 372, 359/368
See application file for complete search history.

(56) References Cited

U.S. PATENT DOCUMENTS

| 4,188,122 | A | * | 2/1980 | Massie et al. | ............... 356/489 |
|---|---|---|---|---|---|
| 4,621,911 | A | * | 11/1986 | Lanni et al. | ................ 350/524 |
| 4,813,782 | A | * | 3/1989 | Yagi et al. | ................... 356/507 |
| 5,715,060 | A | * | 2/1998 | Sides | ......................... 356/623 |
| 6,424,421 | B1 | * | 7/2002 | Cremer et al. | .............. 356/620 |
| RE38,307 | E | * | 11/2003 | Gustafsson et al. | ......... 359/385 |

\* cited by examiner

*Primary Examiner*—Bradley L. Sisson
(74) *Attorney, Agent, or Firm*—Davidson, Davidson & Kappel, LLC

(57) ABSTRACT

The present invention relates to two new wave field microscopes, type I and type II, which are distinguished by the fact that they each have an illumination and excitation system, which include at least one real and one virtual illumination source, and at least one objective lens (in the case of type II), i.e., two objective lenses (in the case of type I), with the illumination sources and objective lenses being so positioned with respect to one another that they are suited for generating one-, two-, and three-dimensional standing wave fields in the object space. The calibration method in accordance with the present invention is adapted to this wave field microscopy and permits geometric distance measurements between fluorochrome-labeled object structures, whose distance can be less than the width at half maximum intensity of the effective point spread function. The invention relates moreover to a method of wave-field microscopic DNA sequencing.

14 Claims, No Drawings

WAVE FIELD MICROSCOPE WITH DETECTION POINT SPREAD FUNCTION

BACKGROUND OF THE INVENTION

The invention relates to a wave field microscope having an illumination or excitation system.

By using highly specific labels, such as DNA probes or protein probes, it is possible to label virtually arbitrarily small (sub)structures, in biological (micro-)objects, especially in cells, nuclei, cell organelle, or on chromosomes,—referred to in the following simply as objects. Structures can be specifically represented in dimensions of a few μm ($10^{-6}$ m) up to a few tens of nm ($10^{-9}$ m). The labels are usually coupled to fluorochromes, or also to colloidal (gold) microparticles, to facilitate their optical detection and image formation, i.e., to render them possible in the first place.

To be able to detect two labels within the same object, separately from one another, the labels in question are often coupled to heterochromatic fluorochromes. The available color emission spectrum of the fluorochromes usually used ranges from deep blue, through green, red, and up to the infrared spectral range. However, fluorochromes can also be used, which are neither differentiated in their excitation spectrum, nor in their fluorescence spectrum, but whose fluorescence emission lifetime is used as a distinguishing parameter.

The advantage of the latter is that wavelength-dependent focal shifts do not occur. Fluorochromes can also have different emission spectra and, thus, varying spectral signatures, but be excitable by the same photon energy, e.g., by multiphoton processes. Here as well, one can avoid wavelength-dependent focal shifts in the excitation between fluorochromes having different spectral signatures.

The aforementioned fluorochromes that are able to be or are bound to specific (substructures in biological microobjects are designated in the following as fluorescence labels.

If the excitation spectra and/or emission spectra and/or the fluorescence lifetimes of two fluorescence labels match, then these fluorescence labels have the same spectral signature with respect to the parameter in question. If the fluorescence labels differ in one or more parameters relevant to the measurement, then they have different spectral signatures.

Fluorescence is understood in the following to be any photon interaction, in which differences arise between the excitation spectrum and the emission spectrum of the same substance that are not attributable to monochromatic absorption or dispersion. This also includes, in particular, multiphoton interactions, in which the excitation wavelengths can be greater than the emission wavelengths.

The concept of fluorescence is used here as well for the narrowly related phenomena of luminescence, in particular for phosphorescence. This includes, in particular, longer average fluorescence lifetimes, e.g., fluorescence lifetimes in the range of up to several or many msec (milliseconds). The closely related processes of luminescence, phosphorescence, and fluorescence are considered in the following as having equal relevance to the present invention.

Fluorescence labels in spatially extended biological objects are detected, imaged, and quantitatively localized with respect to defined object points/object structures (distance and angular measurements) using light-microscopic measuring methods. A decisive role is played in this connection by the so-called "point spread function"=PSF or "point response" of the microscope used, or generally of the optical system, i.e., its ability to construct from an "ideal punctiform" object, an equally ideal punctiform image. The point spread function is a characteristic feature of every imaging optical system, and a measure of its quality.

Distance measurements between object structures depend substantially on the effective point spread function—i.e., that given locally in the labeled object point. This effective point spread function, in turn, is considerably dependent on the specific local refractive index and the absorption in the object, in the object's embedding medium, in the immersion fluid and, in some instances, in the cover slips.

Generally, the effective point spread function clearly differs from the point spread function calculated for the microscope employed. As a rule, the point spread functions measured under technically optimized marginal conditions also differ from the effective point spread functions attainable in biological objects under practical, routine laboratory conditions.

Since, for the most part, these effective point spread functions are not available, to calibrate distance measurements, one reverts to ideal, calculated results or to calibration measurements performed under typical conditions, such as reflection methods. However, both methods are detrimental to precision in the case of three-dimensional distance measurements in biological micro-objects. Consequently, there is considerable uncertainty in determining the actual spatial distance between the object structures. In the case of biological objects, such quantitative size estimations contain uncertainties of up to several micrometers.

Up until recently, the virtually unanimous conviction prevailed in the scientific community that two object structures can only be separated if they are spaced apart by at least the width at half maximum intensity of the effective point spread function.

It was not until 1996 that the originators of the present invention succeeded in devising a calibration method which is not necessarily prior art to the present application for distant field microscopy (and also flow fluorometry), making it possible for high-precision distance measurements to be made between object structures, which are spaced apart by a distance smaller than the resolution of the distant field microscope in question, i.e., smaller than the width at half maximum intensity of the effective point spread function, independently of the position of the object structures in question in the three-dimensional space.

This method includes the following steps:

Before, during, or after preparing the object in question on or in an object holder, in particular a slide, object carrier fiber, object carrier capillary tube, or object carrier fluid, the structures (measuring structures) to be examined or to be localized are labeled with fluorescent stains having different and/or the same spectral signatures, i.e., such structures to be localized (measuring structures) directly proximate to one another, namely within the width at half maximum intensity of their effective point spread function, are labeled with fluorescent stains having different spectral signatures, while such measuring structures, whose distance from one another is greater than the width at half maximum intensity of the effective point spread function, are labeled with fluorescent stains having different or the same spectral signatures. Two measuring structures to be localized may then always be labeled with the same spectral signature, when they can be clearly identified, for example, by their relative position or by other criteria.

Calibration targets of a defined size and spatial arrangement are labeled with the same fluorescent stains;

the fluorescing calibration targets are either prepared together with the objects, or separately on or in the/an object holder (slide, object carrier fiber, object carrier capillary tube, object carrier fluid, or the like).

The (specimen) object and calibration targets are examined under identical conditions, simultaneously or sequentially, microscopically or flow-fluorometrically.

Two defined calibration targets having different spectral signatures are measured at a time under consideration of the wavelength-dependent imaging and localization properties of the particular optical system (microscope or flow-fluorometer). The measured values ascertained in the process, equivalent to the actual values, are compared to the previously known, actual distance values, equivalent to the reference values (i.e., to the reference localizations calculated on the basis of the geometry), and the difference between the actual values and reference values, namely the calibration value, is used to correct the shift, which is conditional upon the optical system, in the detection of various emission loci, in particular of the measuring structures.

In other words: the distance measurement is performed between the object (sub)structures labeled (depending on the proximity to one another) with different or same spectral signatures—in the following, also referred to as measuring structures—on the basis of the highly precise localization of independent (calibration) targets having corresponding spectral signatures and having known sizes and spatial configurations, under consideration of the wavelength-dependent imaging and localization properties of the particular optical system, the calibration measurements taking place between the (calibration) targets, and the measurements taking place in the biological objects, under the same system and marginal conditions. These calibration targets have the same or a higher multispectral quality than do the (object) structures to be measured. They can be arranged directly in the biological objects or be present as separate preparations on an object holder (slide or object carrier fiber/capillary tube or object carrier fluid, or the like), or be part of an object holder. One can discriminate between two or more fluorescing measuring structures in intact, three-dimensional biological objects, whose spacing and spatial extent is smaller than the width at half maximum intensity of the effective point spread function, on the basis of their differing spectral signatures (fluorescence-absorption wavelengths and/or fluorescence-emission wavelengths and/or the fluorescence-emission lifetimes), i.e., one can determine the distances between them.

The distance measurement is reduced to the localization of the individual structures to be measured and can be performed—at this point, using optical distant field microscopy or flow fluorometry, as well—with a substantially higher precision than the width at half maximum intensity of the point spread function. The localization of the point of concentration of the measuring structures in question is adapted to the maximal intensity of their fluorescence signal. This means that, from the measured (diffraction-limited) signal (=intensity curve) of a fluorescent point (=fluorescing measuring structure),—under consideration of the composite information from the primary and secondary maxima— the point of concentration (bary center) of the signal is determined and, thus, the location of the measuring structure. When working with optical systems that are free from defects and, consequently, with ideal symmetry of the measured intensity distribution (=characteristic of the intensity curve), the point of concentration (bary center) of the intensity curve colocalizes, within the localization accuracy, with the primary maximum (=maximum 0 order of the diffraction image) of the measured intensity distribution.

With this new calibration method, optical distant field microscopy, such as wave field microscopy (or also scanning flow fluorometry) can be used to measure geometric distances in biological micro-objects, whereby the distances to be determined can be smaller than the width at half maximum intensity of the effective point spread function in the object. Since the information content of the distance determinations performed therewith corresponds to a distance measurement obtained at an increased resolution, one can (and will in the following) also speak in abbreviated form of "resolution equivalent".

Using multispectral calibration, one can perform in situ measurements at the specific biological object, on the basis of the system's imaging properties. When the fluorescence lifetime is used as the sole parameter type and/or the fluorochromes are excited with the same photon energy (energies), the calibration eliminates the need for in situ correction of the chromatic shift in the object plane. This calibration method renders possible three-dimensional, geometric distance measurements in biological objects, all the way down to a level of molecular precision (i.e., resolution equivalent better then 10 nm), for the highest resolving distant field microscope types, such as the wave field microscope, and given the use of suitable fluorescence labels.

To determine the actual and reference values, for comparison thereof, and to define the correction value/calibration value, the following method steps are preferably carried out:

one or a plurality of calibration targets B having a distance greater than the width at half maximum intensity of the effective point spread function from the point of concentration of the N measuring structures is/are labeled with any desired spectral signature;

the distances $d_{ik}$ (i, k=1 . . . N, i≠k) of the points of concentration of the spectrally separated diffraction figures of the N measuring structures, and the distances $d_{iB}$ of the N measuring structures from the calibration target B are measured, automated methods for image analysis being applied;

for one measuring structure, the segments $d_{ik}$ and $d_{iB}$ are each measured in the plane of the narrowest point spread function, as are remaining distances, for which the object is rotated in each instance axial-tomographically by a defined angle $\Phi_m$;

optical aberrations from the calibration measurements are corrected and, in each case, a cosine function $A_{ik} \cos(\phi_m + \theta_{ik})$ or $A_{iB} \cos(\phi_m + \theta_{iB})$ having suitable phase shift is adapted to the corrected measured distances $d_{ik}(\theta_m)$ and $d_{iB}(\theta_m)$;

the maxima $A_{ik}$ and $A_{iB}$ of the adaptation function of $d_{ik}$ or $d_{iB}$ are divided by the magnification factor and determined as the Euclidian distance $D_{ik}$ or $D_{iB}$ of the N measuring structures, from one another, or of the distances of the measuring structures to reference point B.

To determine the maxima, one preferably draws additionally on the corresponding minima of the distance $z_{ik}$, $z_{iB}$ in the plane orthogonal to the plane of $d_{ik}$, $d_{iB}$, and subjects them to analog analysis.

All coordinates of the N measuring structures and their relative coordinates to reference point B, i.e., positions $x_i$, $y_i$, $z_i$ and $x_k$, $y_k$, $z_k$, or distances $x_k-x_i$, $y_k-y_i$, $z_k-z_i$ and $x_B-x_i$, $y_B-y_i$, $z_B-z_i$ are determined in accordance with the present invention on the basis of the microscopically measured 3D distances $D_{ik}$ or $D_{iB}$, preferably using the following system of equations $$D^2_{ik}=(x_k-x_i)^2+(y_k-y_i)^2+(z_k-z_i)^2$$

$$D^2_{iB}=(x_B-x_i)^2+(y_B-y_i)^2+(z_B-z_i)^2$$

$$D^2_{kB}=(z_B-x_k)^2+(y_B-y_k)^2+(z_B-z_k)^2$$

To guarantee the ascertained measuring results, the procedure described above should be carried out for a plurality of calibration targets B and for the same N measuring structures.

The coordinates and distances of the N measuring structures can be determined on the basis of the points of concentration, which are derived from the barycentric averages of the measurements for all reference points.

For graphical representations in particular, the ascertained positions $x_i$, $y_i$, $z_i$ and $x_B$, $y_B$, $z_B$ preferably undergo convolution using a point spread function, whose half width is that of the resolution equivalent achieved in each instance.

For the fluorochrome labeling of measuring structures and of calibration targets, preferably those fluorochromes are used which can be excited in the ultraviolet, visible and/or infrared light wavelength range, and which emit in the ultraviolet, visible and/or infrared light wavelength range. As calibration targets, one can use either biological calibration targets or non-biological, i.e., synthetic calibration targets.

The biological calibration targets are labeled regions of the biological object whose proximity to one another is known. The region(s) in question can, for example, be labeled using suitable biochemical probes. The practical advantage of using such biological calibration targets over synthetic calibration targets, for example calibration spherules, is that in performing the calibration, besides the optical marginal conditions of the object, marginal effects that are conditional upon the specimen also enter into the calibration, such as the actual fluorescence signal's relationship to the non-specific background (which is determined by automatic image analysis algorithms).

Especially suited as non-biological, i.e., synthetic calibration targets are micro-spherules, which have the same or a higher multispectral signature than the measuring structures to be localized. They are handled in the same way as the biological objects.

Calibration targets of this kind are preferably fixed to object holders in a defined spatial arrangement. This can be done already at the time that the slide in question is fabricated, which is particularly advantageous for routine use. To rectify the problem encountered with all known distant field microscopy methods, that the width at half maximum intensity of the point spread function and, thus, the resolution limit is dependent upon the relative position in the space, i.e., for example, normal to the optical axis (=lateral) it is narrower than in the direction of the optical axis (=axial), the mentioned calibration method can be easily combined with the so-called micro-axial tomography methods known in the related art. In these micro-axial tomography methods, the (biological) objects are arranged in capillary tubes or on glass fibers and in, i.e., under the microscope, definably rotated about an axis, which is usually normal to the optical axis of the microscope, distance measurements being carried out in that direction which has the narrowest width at half maximum intensity of the effective point spread function.

A distant-field light microscopy method which is particularly suited for detecting and imaging especially very small, fluorescently labeled substructures, in biological objects, is the wave field microscopy method. This method has the advantage over the known epifluorescence microscopy methods and or confocal laser scanning microscopy, that it renders possible depth discrimination—normal to the wave fronts—, in the axial direction as well. Thus, it makes it possible to have substantially improved resolution (at a higher numerical aperture, its dimensions can be substantially smaller than the wavelength of the light used for excitation).

In wave field microscopy, as described, for example, in U.S. Pat. No. 4,621,911, fluorescing, i.e., luminescing specimens are illuminated in the optical microscope by a standing wave field (standing wave field fluorescence microscopy, SWFM). A standing wave field is formed (only) where there is superposition of light that is capable of coherence. The specimens are arranged in a zone of equidistant, plane wave fronts, and excited to emit fluorescence or phosphorescence. The spacing of the wave fronts and their phases can be varied (in particular to produce images). The three-dimensional distribution of the fluorescent, i.e., luminescent object points can be reconstructed from the individual optical sections using computer-image processing.

The plane wave fronts are arranged normal to the optical axis of the detecting objective lens and are produced through coherent superposition of two laser beams at a defined angle q to the optical axis of the microscope system, the angle q defining the spacing of the wave fronts from one another—at a given wavelength and index of refraction. In place of two intersecting laser beams, the wave field can also be produced by forcing a laser beam, after suitable reflection, at a specific angle (for example, using a reflector), into interference with itself. The plane wave fronts are distinguished by the fact that the intensity profile is (co-) sinusoidal in the direction normal to the wave fronts.

The fluorescence, i.e., luminescence is either spectrally discriminated through suitable optical filters and conducted in various beam paths, or detected confocally. The attainable resolution, i.e., the smallest still measurable distance between two punctiform object structures, which are labeled by fluorochromes having the same spectral signature, is given either by the Abbe criterion (=the maximum 0 order of the diffraction image of a point object is localized in the $1^{st}$ minimum of the diffraction image of a second point object) or is given by the width at half maximum intensity of the effective point spread function. It is dependent upon the particular wavelength, the numerical aperture of the objective lens employed, as well as upon the local refractive indices of the objects, of the embedding medium, of any cover slips used, and of any immersion fluids used.

In principle, the known wave field microscopes have the following design: they include (I) an illumination, i.e., excitation system, made up of at least one real and one virtual illumination source, and at least one objective lens, so allocated to one another that they are able to produce a one-dimensional, sinusoidal, standing wave field;

(II) an object space, including holding and maneuvering devices for the object; and (III) a detection system, made up of at least one objective lens, at least one eyepiece, and at least one detector, this often being a camera, in particular a CCD camera, which is positioned with the CCD chip in the intermediate image plane.

A drawback of this related-art wave field microscope, referred to in the following as "one-dimensional wave field microscope" ("SWFM"), i.e., of the wave field microscopy method that can be implemented with the microscope is that the periodically generated wave field (in the case of epifluorescent detection, in conjunction with optical sectioning methods) leads to an ambiguity in the observation or imaging of an object structure, whose extent in the direction normal to the wave fronts is substantially greater than $\lambda/2n$ ($\lambda$=wavelength of the excitation, n=effective index of refraction). This ambiguity initially makes it more difficult to effectively benefit from the improved resolution achieved with the interference pattern.

To implement distance measurements and other examinations of the spatial relationships of three-dimensional objects, one can combine the known distant field microscopy methods, inclusive of one-dimensional wave field microscopy, with axial tomography. For this, the biological objects to be examined, in some instances after being furnished with calibration targets, are prepared as specimen in or on a micro-capillary tube or glass fiber, used as object holders or slides. The capillary tube/fiber has a precisely defined diameter, varying diameters being possible. To localize this capillary tube/fiber on the microscope table, a special mount fixture is proposed, which is made of a rigid, preferably dorsiventrally flattened frame, at or on which is mounted at least one bearing sleeve, in which a micro-capillary tube or glass fiber can be rotationally supported (preferably with the axis of rotation normal to the optical axis of the microscope). (The bearing sleeve(s) should be arranged in such a way that the axis of rotation of the capillary tube/fiber is normal the optical axis of the microscope.) The rotation of the specimen objects in or on the capillary tube/fiber follows directly from rotation of the capillary tube/fiber, preferably with the assistance of a torque motor.

SUMMARY OF THE INVENTION

The object of the present invention is to further refine a wave field microscope of the known type so as to render it suitable for generating plane wave fields in more than one dimension, accompanied by a high variability of the distances of the interference maxima, and to further refine the aforementioned calibration method so that it can be employed in combination with such a wave field microscope. It is, moreover, the aim of the present invention to devise a method for wave-field microscopic DNA sequencing.

This objective is achieved, on the one hand, by providing the so-called "multi-dimensional wave field microscope", described in the following, and, on the other hand, by providing the calibration method, likewise described in the following, which is adapted to the application of a multi-dimensional wave field microscope. Moreover, a method is provided for "fluorescence DNA sequencing".

A "multi-dimensional wave field microscope" (type I) in accordance with the present invention is a wave field microscope of the type mentioned at the outset, which is characterized by the features listed in the following:

(1) The illumination, i.e., excitation system includes, in two or all three spatial directions, at least one real or virtual illumination source for light beams, capable of coherence, and at least one reflector or beam splitter for decoupling beam components, or a further illumination source for light beams, capable of coherence, to each of which is assigned at least one objective lens, and which are each suited for generating light wave trains, the light wave trains of the one illumination source being aligned antiparallel or in variably adjustable angles to the light wave trains of the reflector, i.e., of the other illumination source, and in fact such that the light wave trains emitted by the one illumination source interfere with those of the reflector, i.e., of the other illumination source to form a standing wave field having plane wave fronts.

(2) The detection system includes at least one detection objective lens, suited for epifluorescent detection, and/or at least one detection objective lens, which is suited for raster scanning point detection and preferably has a high numerical aperture, and which is arranged with its optical axis normal to the wave fronts of one of the interfering wave fields, and which can be identical to one objective lens of the excitation system. Arranged upstream from the detection objective lens suited for epifluorescent detection is a flat (two-dimensional) detector, e.g., a camera, while the detection objective lens suited for raster scanning point detection has at least one stationary, confocal detection annular plate and/or aperture plate, and/or at least one stationary detection slit arranged upstream from it, and a point detector, in particular a photomultiplier, a photodiode, or a diode array arranged downstream from it.

Here, "high" numerical aperture is understood to be a numerical aperture $\geq 1$ and "low" numerical aperture is understood to be a numerical aperture $<1$.

In one especially preferred specific embodiment of this wave field microscope (type I), in at least one spatial direction, an objective lens of a low numerical aperture or a reflector is assigned to an objective lens of a high numerical aperture, and in one or both other spatial direction(s), either two objective lenses of a low numerical aperture or an objective lens of a low numerical aperture and a reflector are assigned to one another.

The other "multi-dimensional wave field microscope" (type II) in accordance with the present invention is a wave field microscope of the type mentioned at the outset, which is characterized by the following features:

(1) The illumination, i.e., excitation system includes, in at least one of the three spatial directions, at least one real or virtual illumination source for light beams, capable of coherence, and at least one beam splitter for decoupling at least one beam component, to which is assigned a common objective lens, into which the light beams, i.e., light wave trains of the illumination source(s) and of the beam splitter(s) can be launched in such a way that they produce on the rear focal plane (facing away from the object space) two spaced apart focal points, and that they run relatively to each other in a variably adjustable angle in the space between the two focal planes, and interfere to form a one-dimensional, standing wave field.

(2) The detection system includes at least one detection objective lens, suited for epifluorescent detection, and/or at least one detection objective lens, which is suited for raster-scanning point detection and preferably having a high numerical aperture, which can also be identical to the objective lens of the excitation system. Arranged upstream from the detection objective lens suited for epifluorescent detection is a flat (two-dimensional) detector, e.g., a camera, while the detection objective lens suited for raster-scanning point detection has at least one stationary, confocal detection annular plate and/or aperture plate, and/or at least one stationary detection slit arranged upstream from it, and a point detector, in particular a photomultiplier, a photodiode, or a diode array arranged downstream from it.

In one preferred specific embodiment of this wave field microscope (type II), the illumination, i.e., excitation system has in the same or in one of the two other spatial direction(s), in each case, at least one further real or virtual illumination source for light beams, capable of coherence, and/or at least one beam splitter for decoupling at least one beam component, to which is assigned in each case a further objective lens, through which the light beam(s) (light wave trains) are focused into the object space and are aligned in such away that they interfere with the light beams from the same or from the other or two other spatial direction(s), i.e., with the one or two-dimensional wave field formed by these, to form a two- or three-dimensional wave field.

It is a feature of another, very advantageous further refinement of all aforementioned wave field microscopes (type I and type II) in accordance with the present invention that the object space includes an object mount fixture, in or on which the object is rotatably supported with the measuring structures, and/or, if indicated, with the calibration target(s), in the wave field, about one or two axes running orthogonally to one another, a rotational capability of about 360 degrees ($2\pi$) being preferred for at least one axis.

Using these multi-dimensional wave field microscopes type I and type II, a plurality of object planes can be detected time-sequentially and/or simultaneously, through one, two and/or three objective lenses (i.e., to their orthogonal axes). Precision distance measurements of point objects having the same or different spectral signatures, whose spacings are smaller than the widths at half maximum intensity of the effective point spread functions, can be undertaken in (all) spatial directions.

The stationary, confocal detection annular plate(s), aperture plate, and/or the stationary detection slit(s), in combination with at least one suitable light intensity detector, make it advantageously possible for the object to be raster-scanned in the x-, y-, and z-direction through the wave field (object or stage scanning).

Above and beyond this, the wave field microscope type II in accordance with the present invention, and the wave field microscopy that can carried out with it, have the advantage—particularly over the known one-dimensional wave field microscopy—that both the lateral resolution (i.e., normal to the optical axis), as well as the axial resolution are substantially improved. For the first time, one is able to discriminate planar objects in the axial direction without using confocal systems. Moreover, it is advantageously possible for one to shift the object in the lateral direction during the observation, i.e., for recording/data registration purposes. With the aid of image processing and reconstruction methods, a higher lateral resolution is then able to be achieved from the thus obtained multiple recordings. The design in accordance with the present invention of type II, including an objective lens, is additionally suited for generating a one-dimensional wave field normal to the optical axis of an epifluorescence microscope and, thus, for improving the lateral resolution of the same.

In another design variant of this "multi-dimensional wave field microscope" (type I and/or type II), the illumination source(s) producing the multi-dimensional wave field, and/or the reflector(s), and/or the beam splitter(s), and/or the objective lens(es) and, thus, the multi-dimensional wave field, are rotationally arranged or mounted about one or two axes running orthogonally with respect to one another.

To project the image of the lateral object regions of a stationary object in the two- or three-dimensional wave field, onto the detector annular plate, detector aperture plate, or the detector slit, each wave field microscope (type I and/or type II) in accordance with the present invention can be equipped with a scanner reflector, arranged to form an image of the lateral object regions in question with the desired, mostly maximal, fluorescence intensity.

In one particularly advantageous further refinement of the multi-dimensional wave field microscope according to the present invention (type I and/or type II), which is suited for two- or multi-photon fluorescence excitations, the so-called "wave field microscopes having combined multi-photon fluorescence excitation", the illumination system in question includes in at least one of the three spatial directions, a real illumination source for the two- or multi-photon excitation, and in one or both other spatial direction(s), a real and/or virtual illumination source for the two- or multi-photon excitation. The standing wave fields ($WF_1, WF_2, \ldots, WF_i$) generated with it have wavelengths ($\lambda_1, \lambda_2 \ldots, \lambda_i$) which differ from one another, and the distances ($d_1, d_2, \ldots, d_i$) between their specific wave maxima or wave minima amount to $d_1 = \lambda_1/2n \cos \theta_1$ or $d_2 = \lambda_2/2n \cos \theta_2$ or $d_i = \lambda_i/2n \cos \theta_i$ (where: n=the index of refraction in the object space, $\theta_1, \theta_2, \ldots \theta_i$=the intersection angle of the light wave train of the wavelength $\lambda_1, \lambda_2 \ldots, \lambda_i$ with the optical axis). In accordance with the present invention, these wave fields $WF_1, WF_2 \ldots W_i$ are aligned in such away with respect to one another that at least a maximum of two or of all standing waves is situated at the same place, namely the location of a multi-photon excitation.

Suitable illumination sources for the two- or multi-photon excitation are known in the related art and described, for example, in the publication by W. Denk, J. H. Strickler, W. W. Webb, "Two-Photon Laser Scanning Fluorescence Microscopy", Science, vol. 248, pp. 73-76 (Apr. 6, 1990), to whose content reference is expressly made here. These illumination sources produce either photons of varying wavelengths or coherent photons of the same wavelength.

One particular advantage derived from the combination of one- and two- or multi-photon excitation is the simultaneous excitation of fluorescence labels having different spectral signatures. This makes it possible to eliminate errors in the distance measurement caused by chromatic aberrations in the object. In the two-photon excitation, a fluorochrome molecule is excited when two photons simultaneously supply the energy for exciting one molecule. In this context, the two photons participating in the excitation of the molecule can have the same or different wavelengths or energies. For a coincident excitation with different wavelengths ($\lambda_1, \lambda_2$) in the case of the so-called "two-photon wave field microscopy", two wave fields having the wavelengths $\lambda_1$ and $\lambda_2$ must be established in each specific spatial direction. In this context, the wave maxima or the wave minima of the two standing wave fields (WF1, WF2) have the distances $d_1 = \lambda_1/2n \cos \theta_1$ or $d_2 = \lambda_2/2n \cos \theta_2$ (whereby it holds that: n=index of refraction in the object space, $\theta_1, \theta_2$=intersection angle of the laser beam of the wavelength $\lambda_1, \lambda_2$ with the optical axis). Since distances $d_1$ and $d_2$ are generally different, the two wave fields are so aligned per spatial direction that a primary maximum of both standing waves is situated at the same location. Multi-photon effects can only occur where both wave fields are superimposed on one another. Thus, it is only individual "streaks" in the wave field of one spatial direction which are still used for the multi-photon excitation. Ambiguities in objects having dimensions greater than d do not occur until dimensions meet the condition $k_1 d_1 = k_2 d_2$ ($k_1$, $k_2$ are integral numbers). Thus, any ambiguity in three-dimensional imaging is eliminated by a multi-photon excitation of the fluorescence-labeled measuring structures and of the calibration targets. Employing two- or multi-photon fluorescence excitation methods renders possible a more rapid scanning or raster-scanning of the object, i.e., of the points, lines and planes of the object and, thus, an improved imaging quality, particularly when working with moving objects as well.

A likewise very advantageous further refinement of the multi-dimensional wave field microscope according to the present invention is distinguished by the fact that an arrangement made up of a light source, objective lens, and an electrically conductive reflector, which is suited for generating a one-dimensional, electrical wave field, is provided relative to the object-carrier mount fixture, and, in fact, so as to enable the measuring structures located in the object and/or calibration targets (for example, when situated on or in molecule chains), when necessary, to be aligned through application of the electrical field—prior to or during the microscopic measuring operation. (The molecule chains that are spatially aligned in this manner can then still be subsequently fixed using immobilizing substances.) This variant of the wave field microscope according to the present invention is suited, above all, for wave-microscopic DNA sequencing, the one-dimensional electric wave fields being used for calibration during DNA sequencing.

To detect the luminescent light, a CCD camera(s) is preferably used, in a generally known way. This camera can be located behind the detector annular plate or aperture plate or the detector slit. In place of the CCD camera or the CCD chip, the multi-dimensional wave field microscope in accordance with the present invention can also be equipped, however, with an electronic image-recording device, as known, for example, from the related-art confocal laser scan microscopes (CLSM). In principle, in accordance with the present invention, each light-sensitive detection unit, in particular photodiode(s), photomultipliers, CCD cameras/chips, CCD arrays, avalanche diodes, (avalanche) diode arrays, two-dimensional (avalanche) diode matrices, can be arranged behind the detector annular plate or aperture plate or the detector slit, to detect and document the fluorescence, it also being possible to undertake the fluorescence lifetime measurements.

The calibration method in accordance with the present invention is a calibration method of the aforementioned type, and is characterized by the following measures:
(1) The biological object having the fluorochrome-labeled measuring structures, and/or the fluorochrome-labeled calibration target(s), is sequentially or simultaneously illuminated by individual (separate) standing wave fields, running orthogonally to one another in two or three spatial directions, and interfering with one another to form a two- or three-dimensional wave field, the fluorochromes being excited to emit fluorescence.
(2) To detect the fluorescence intensity, a camera and/or one or more two-dimensional arrangement(s) of individual detectors, each having a circular, annular, or slit-shaped plate, or an arrangement of a plurality of circular, annular, or slit-shaped plates is used.
(3) Either the object having the measuring structures and/or the calibration target(s) or the one- or two-dimensional wave fields, or both, is rotated during the measuring operation step-by-step about one axis or about two axes running orthogonally to one another, the fluorochrome-labeled measuring structures and/or calibration targets being sequentially or simultaneously illuminated by one or two individual standing wave fields disposed orthogonally to one another.
During the simultaneous illumination, the micro-object having the measuring structures and the calibration target(s) are fixedly or rotationally mounted about an axis. Two or three standing, plane wave fields running orthogonally to one another are forced into interference and simultaneously illuminate the micro-object. Two wave fields form planes having a two-dimensional, symmetric grating of points of maximal and minimal intensity. Three wave fields result in the formation of a three-dimensional spatial grating of symmetrical, evenly spaced points of maximal and minimal intensity. A continuous intensity profile is evident between the intensity maxima and minima. In the case of sequential illumination, the micro-object is rotated in the wave field about two axes. The position of the wave field can be varied relative to the object during or following the detection.

Through the use of suitable fluorescence labels, the present invention thus renders possible three-dimensional (3D) geometric distance measurements between fluorescence targets having the same or different spectral signatures, with molecular precision, i.e., with a 3D resolution equivalent of up to better than 10 nm, and with a 3D localization accuracy of up to better than 1 nm. In contrast to electron microscopy or to optical and non-optical near-field microscopy, the three-dimensional structure of the object to be examined remains intact, since the need is eliminated for mechanical sections. Thus, 3D distance measurements can be undertaken within a range smaller than the width at half maximum intensity of the effective point spread function in three-dimensionally conserved micro-objects. In particular, the method opens up the possibility of performing three-dimensional distance measurements under vital conditions of the biological object, as well. In DNA sequencing, one can eliminate the need for producing gels and for electrophoretically separating DNA fragments. In the same way, one can do without an autoradiography, since no radioactive tagging is performed. Long DNA sequences (e.g., >1 kbp) can also be easily analyzed.

Moreover, this variant of the method according to the present invention also permits a substantially improved determination of morphological dimensions (for example, volumes, surface areas), to the extent that the multispectral fluorescence labels are properly distributed, for example on the surface of the object. In this manner, for example, the volume of a spherical micro-object having a radius of a few 100 nm can be determined in a substantially improved manner than is possible using conventional morphological segmenting techniques, such as Cavalier and Voronoi methods, or also volume-conserving gradual thresholding methods.

Using the multi-dimensional wave field microscope(s) (type I and/or type II) in accordance with the present invention and the calibration method in accordance with the present invention, it is possible to perform a microscopic DNA sequencing. For this, the "wave field microscopy method for DNA sequencing" in accordance with the present invention is proposed, as described in the following:
(1) All complementary subsequences of the DNA sequence to be analyzed are produced in such a way that all subsequences begin at the same nucleotide of the sequence to be analyzed.
(2) The fragments to be analyzed are all tagged at the 3' end with a reference fluorochrome label α and at the 5' end and/or at defined intermediate locations with a fluorochrome label a, g, c, or t—depending on whether the nucleotide base includes adenine (label a), guanine (label g), cytosine (label c) or thymine (label t)—, the fluorochrome labels a, g, c, t and α having different spectral signatures, and each containing one or a plurality of fluorochrome molecules.

(3) The tagged DNA subsequences are fixed to a carrier in such a way they are present as a linear sequence, and are placed in a one- or multi-dimensional wave field microscope.

(4) The linear DNA subsequences are so oriented with respect to the standing wave fronts, that a precise distance measurement (accuracy $\leq 1 \cdot 10^{-10}$ m) can be implemented between α and a or g, c or t—once the intensity bary centers are defined and the imaging properties are calibrated—; in that (5) the signals of the fluorochrome labels are registered step-by-step, as spectrally separated signals; and (6) from the distances of the fluorescent labels and their spectral signatures, the DNA base sequence of the DNA fragments to be analyzed is determined.

Using this method, which is a completely new kind of method in the related art, the length of DNA fragments can be measured accurately in terms of nucleotides, and their base sequence can also be precisely determined. The need for gel electrophorese and subsequent band analysis is eliminated.

DETAILED DESCRIPTION OF THE PREFERRED EMBODIMENTS

Exemplary and comparison embodiments for further elucidation of the present invention:

Example 1

Design of a Multi-Dimensional Wave Field Microscope Type I Having a Rotationally Supported Object One begins with a conventional "one-dimensional" wave field microscope, constructed, for example, with two mutually opposing objective lenses of a high numerical aperture, or with one objective lens which is higher than an objective lens of low numerical aperture, or with one objective lens for two interfering laser beams. Through the objective lenses, two beam components of one laser are forced into interference so as to form a one-dimensional, standing wave field. The fluorescence is detected by way of one or two objective lens(es) of high numerical aperture. Two further beam components of the laser are launched at a time, in one or in both orthogonal directions to the optical axis of the detection objective lens, via objective lenses of a low numerical aperture and/or focusing lens systems, at an appropriate distance, and forced into interference in such a way with one another and with the one-dimensional, standing wave field, that a two- or three-dimensional, symmetric intensity pattern of intensity maxima and minima is formed.

To provide a supporting arrangement for the object, a micro-axial tomograph is installed in this "multi-dimensional" wave field microscope.

In axial tomography, instead of the glass slide, a microcapillary tube or a glass fiber is used, which is rotationally supported, and accommodates the (biological) object within it (capillary tube), or suitably supports the (biological) object on it (capillary tube/fiber). The capillary tube/fiber, which is usually arranged normal to the optical axis of the detection objective lens, can be rotated about the fiber axis by a defined angle, manually or using a computer-controlled stepping motor. A rotation by an angle of 360 degrees (2π) is possible. The carrier holder for the capillary tube/fiber is rotationally mounted on a semi-circle. In this context, the axis of rotation runs normal to the optical axis of the detection objective lens. The calibration method according to the present invention and digital image analysis are used in detecting the spatial arrangement of the micro-target and its distance. Ambiguities in intensity profiles, i.e., primary and secondary intensity maxima of fluorescent "point" targets, can be statistically analyzed with the assistance of suitable computer algorithms and, thus, enhance localization precision. When working with spatially extended objects, ambiguities can be minimized through the use of two- or multi-photon excitation with photons of varying wavelengths.

Example 2

Distance Measurement Between Gene Segments of Chromosomes in a Cell Nucleus Using Multi-Dimensional Wave Field Microscopy, the Calibration Method in Accordance with the Present Invention, and, if Indicated, Axial Tomography (I) In a cell nucleus, the chromatin of the individual chromosomes takes up defined partial regions. Within one or a plurality of such chromosomal partial regions, the structures to be localized, i.e., the measuring structures, e.g., small chromosome segments, such as genes or gene fragments, are specifically tagged using a method of fluorescence in situ hybridization known from the related art, and, in fact, with fluorochromes of different specific spectral signatures $M_1$, $M_2$, $M_3$, .... The spacings between the labeling locations (the labeled measuring structures) are smaller than classic resolution, i.e., they are smaller than the width at half maximum intensity of the effective point spread function. The (object) structures (measuring structures) are labeled in such a way that the spectral signatures are represented at the structures to be localized (measuring structures) with virtually the same dynamics.

The biological object is prepared on a glass fiber having an exactly defined diameter, or in a round or rectangular capillary tube of defined dimensions.

(II) To determine the distances, specimens suited for microscopic observation are prepared with calibration targets, and, in fact, under the same physical and chemical experimental conditions as the object, i.e., the object structures to be localized (=measuring structures).

As calibration targets, i.e., as preparations with calibration targets, one uses, for example:

a) Micro-Injectable Spherules of One Spectral Signature (Monochromatic):

The spherules are each labeled in accordance with known methods with a fluorochrome, i.e., monochromatically, and are able to be differentiated on the basis of their size, from the measuring structures (to be localized) in the object. One injects such calibration spherules, which represent the spectral signatures of the measuring structures present in the object, but are otherwise preferably identical (with respect to size, geometry, material constitution, etc.). In other words: one selects the spectral signatures of the measuring structures, as well as of the calibration targets, so that, under the given examination conditions, their fluorescence emissions can be analyzed separately from one another. The monochromatic calibration spherules are injected and fixed in such a way that the individual spherules of different spectral signatures form clusters, directly at the glass fiber surface or capillary wall, preferably in a cross-sectional plane of the fiber or capillary tube. When precision fibers and/or precision capillary tubes are used, the spherules are spaced at defined distances from one another, i.e., from a reference plane, reference axis, or reference line.

b) Micro-Injectable Test Spherules of Multispectral Signatures (Polychromatic) and of the Same Spectral Dynamics:

The spherules are each labeled in accordance with known methods with all spectral signatures occurring in the labeled (object) structures (measuring structures). As a result, they can be injected at arbitrary locations in the biological object to be measured (in this case, the nucleus). There is no need for a reference geometry as recited under a), since the points of chromatic concentration are be localized at the same location for each signature. To distinguish among the labeled (object) structures (measuring structures), the spherules can either belong to another size class or, however, bear an additional spectral signature that does not occur in the measuring structures (in accordance with the specimen preparation protocol).

c) Simultaneously Labeled Chromosome Regions of a Known Distance on a Different Chromosome than the One Borne by the Structures to be Localized (Measuring Structures):

The calibration targets, i.e., the chromosome regions having a known distance from one another, are differently labeled with the assistance of a test combination of DNA sequences, which bear the various spectral signatures. The chromosomal calibration targets can be distinguished from the (chromosome) structures to be localized (measuring structures), for example, on the basis of varying fluorescence intensity, or a different intensity ratio among fluorochromes of different spectral signatures, or through the use of an additional fluorochrome having a deviating spectral signature, which was not used when fluorescence-labeling the measuring target. It is also possible that the calibration targets belong to a different size class, than that of the measuring structures to be localized.

(III) The distance measurements are performed using a multi-dimensional wave field microscope in accordance with the present invention, combined with a photomultiplier and/or camera, and data-processing system. A series of optical sections is recorded from the biological micro-object, in the example here, a cell nucleus. The measuring structures $M_1, M_2, M_3, \ldots M_l$ have $l=1, 2, \ldots, L$ the spectral signatures. The spectral signature of the calibration targets $U_1, U_2, U_3, \ldots, U_l$ differs from that of the measuring structures, e.g., in volume, diameter, intensity, or in the number of spectral signatures ($l=1, 2, \ldots, L+1$). The images of the optical sections are separately recorded for each spectral signature and, in some instances, the background is also corrected. For the analysis, the calibration targets are first identified, and the chromatic shift is determined. For this, the calibration targets are localized under each spectral signature, and the distances between the calibration targets are measured on the basis of fluorochromes labels of different spectral signatures. The measured localizations (i.e., the measured targets distances) are compared to the reference localizations (i.e., the actual target distances) calculated on the basis of the geometry, and from this, the spectrally produced (shift) is determined. This shift is the calibration value for the measured distance values between the (object) structures to be localized (measuring structures).

Since this shift is dependent upon the optical properties of the specimen (e.g., refractive indices in the nuclei and in the specimen medium), the calibration should be carried out in situ. In the present example, this means that the calibration targets should be situated next to the labeled (chromosomal) structures (measuring structures) to be examined in the nucleus.

On the other hand, the distances between the (object) structures to be localized (measuring structures) are localized. In this context, one initially determines the position of the points of concentration of the measured intensity signals, independently of one another, in each spectral signature, i.e., the distances are measured between the various color signals, i.e., color points, of the measuring structures in question, e.g., between the red-fluorescing and the green-fluorescing color point (from intensity maximum to intensity maximum, or from point of concentration/bary center to point of concentration/bary center), and this measured value is corrected with extreme precision by the shift (that is conditional upon the different spectral signature) determined with the calibration targets.

The corrected positions of the measuring structures are specified in relationship to a reference point. This reference point can be, e.g., an arbitrarily designated, fixed point in the object, or the point of concentration of a calibration target (e.g., a labeled chromosome region) or a chromosome territory marked in some other way. However, it can also be the point-of-concentration coordinates of all measuring structures within a chromosome territory.

When calibration targets are used in the form of micro-injectable test spherules having a multi-spectral signature (polychromatic), the chromatic shift is determined from the difference in the localization of the points of concentration for each signature. The fluorescence emission belonging to a calibration target can be identified, as required for this, for example, by applying volume-preserving threshold-value methods or by averaging the segmenting results in the case of threshold-value variation.

When calibration targets are used in the form of fluorochrome-labeled object regions having a multi-spectral signature (polychromatic), the chromatic shift is determined in the exact same way.

Also very suited as fluorochrome-labeled calibration regions are centromer regions, which are hybridized with a probe combination of DNA sequences of the sort which all bind to the same chromosomal DNA sections, but which are labeled with fluorochromes having different spectral signatures. If the hybridization takes place under very stringent conditions, two labeling regions are present per cell nucleus; under not very stringent conditions, additional centromer regions are labeled due to additional secondary binding regions, so that the number of calibration regions rises. This can be quite advantageous.

(IV) The described measuring methods can also be implemented in combination with axial tomography. For this, the biological micro-object, e.g., cell nucleus, in which the measuring structures to be localized are already fluorochrome-labeled and which also already contains calibration targets (for the preparation, see Example 1), is arranged in a glass fiber or in the micro-capillary tube. The axial tomograph is used to rotate the object step by step, by a defined angle, with, in some instances, automatic focusing. A complete two-dimensional or three-dimensional image stack is recorded from each angular step.

The rotation is carried out so as to achieve in each case a maximal distance between two measuring structures, i.e., calibration targets (i.e., between their points of concentration of fluorescence intensity). The maximum measured distance corresponds to the actual distance.

If one is only interested in the distances between the measuring structures, i.e., calibration targets, i.e., not in their absolute spatial arrangements, one can, at this point, continue from one of the known measuring structures, i.e., calibration targets, in order to maximize and determine a distance to a third measuring structure, i.e., to a third calibration target. If the distances between the measuring structures, i.e., calibration targets are greater than the width at half maximum intensity of the point spread function, then one single spectral signature suffices; if, on the other hand, the distances are smaller, the measuring structures, i.e., calibration targets must be distinguished on the basis of their multispectral signature. The points of concentration (maxima) of the signals are used for the localization. To the extent that the diameter of the measuring structures under observation is smaller than the width at half maximum intensity of the effective point spread function, all diffraction images of the measuring structures, i.e., calibration targets are determined by an exacting point spread function, so that the maxima can be optimally determined.

If one is interested in the absolute arrangement of the measuring structures, i.e., calibration targets in the space, then the points of concentration (so-called "bary centers") must be precisely determined. By repeating the entire measuring procedure again and again, and through statistical evaluation, one can improve upon the absolute localization of the measuring structures, i.e., calibration targets, i.e., the angular measurements.

Instead of implementing the above-described calibration and distance measurement between the structures to be localized, i.e., measuring structures, in the same biological object, one can also carry out the calibration independently of the measuring structures, on biological objects of the same kind. In this variant of the method, it is easier to distinguish between the fluorescence signals of the calibration targets and those of the measuring structures. On the basis of the optical shift values determined with the calibration targets, one can plot calibration curves for the distance measurements between the measuring structures. Calibration curves of this kind, for example, provide information about the spectral shift as a function of the index of refraction and absorption of the employed immersion medium, the employed optics, filters and detection units, of the evaluation algorithms used, of the biological objects used, of the localization of the measuring structures, i.e., calibration targets in them, etc. Using information from the special calibration curves for distance measurements in accordance with the present invention is particularly beneficial and those cases where greater precision tolerance is allowed.

Example 3

Examination and Display of Three-Dimensionally Spatially Extended Objects Using Multi-Dimensional Wave Field Microscopy, the Calibration Method in Accordance with the Present Invention and Simultaneous Image Recording A three-dimensional data record is usually acquired from a biological micro-object by sequential registration, e.g., in confocal laser scanning microscopy, by point-by-point or line-by-line scanning of the three-dimensional object volume; a second method is based on registering the fluorescence emission from the object plane by positioning a detector array in the intermediate image plane conjugate to the object plane. Customarily, the position of this intermediate image plane is fixed; to obtain three-dimensional information about the biological object, this object is moved sequentially through the object plane conjugate to the fixed intermediate image plane; each time, a two-dimensional image data record of the fluorescence emission in question is registered; and/or the object is rotated with the assistance of axial-tomographic methods by different rotational angles, the two-dimensional data records of the object plane conjugate to the fixed intermediate image plane being registered each time.

Various disadvantages are associated with this type of sequential registration of object points, object lines, or object planes: for example, if the registration of the three-dimensional data record fades, this can lead to a shift in the three-dimensional points of concentration, determined in accordance of the present invention, of the fluorescence distribution of labeled object points in a specific spectral signature. Another disadvantage lies in the fact that the three-dimensional data recording does not take place quickly enough to ensure a satisfactory image quality when working with objects that are not permanently stable, i.e., moving objects, particularly in the case of in vivo tagging, such as in fluorescence-labeled chromosomal regions in the nuclei of living cells, which, under physiological conditions, can move with speeds of up to a few nm/sec. (average shift).

To also obtain a satisfactory imaging quality when working with moving objects as well, the present invention provides for a simultaneous recording of the three-dimensional data record of a fluorescence-labeled object. For this, the fluorescence light of a given spectral signature emitted by the object is split by optical elements, e.g., the splitter reflectors, into N beam components, and imaged onto N detector arrays, situated in N different intermediate image planes, which are conjugate to N different object planes. A simple estimation on the basis of the imaging equation reveals that, given a simultaneous registration of an object region having 10 µm axial extension and an objective lens of conventional image distance and high numerical aperture, the distances of the intermediate image planes (detector planes) must be varied (as a function of the objective lens employed) e.g., by a range in the order of magnitude of $\leq 20$ cm. Using further N intermediate optics, the N object planes to be registered for high-precision distance measurements in relevant object regions can also be imaged onto various regions of the same, properly dimensionally sized detector arrays (i.e., onto L<N detector arrays). In this case, one of the N conjugate object planes corresponds to a specific segment of the luminescence detector array(s). For example, a small object region having an extent of a few µm is initially roughly positioned for measuring in wave field microscopy in such a way that its point of concentration is more or less situated in the center of the observation volume of the microscope objective lens used for the registration, as given by the detection point spread function for a specific (intermediate) image plane $B_0$; the fluorescence light emanating from the three-dimensional object is separated in accordance with its spectral signatures and split into N beam components, which are imaged onto N detector arrays (each, e.g., of 8×8, 16×16 or 64×64 pixel size), whose positioning permits the registration of the fluorescence emission from N conjugate object planes by the maximum of the detection point spread function (in relationship to the image plane $B_0$). For example, when objects, each having a distance of 20 nm, are simultaneously recorded following a simple estimation under the above assumptions, shifts in the conjugate intermediate image planes by, in each case, a few 100 µm (near the maximum of the point spread function) are required; i.e., correspondingly small, individual optical corrections are to be carried out, with simultaneous detection of the relevant object segments on one single (or L<N) detector array(s) corresponding to the number of pixels. When the fluorescence emission is split, e.g., into N=20 beam components of the same intensity, the photon number registered from each of the N=20 detector array(s) (or segments) per unit of time is reduced by more or less the same factor. The localization accuracy of a flourescence-labeled object is then reduced on the basis of the degraded photon statistics by, it is estimated, a factor of $\sqrt{20}$. This drawback can be overcome by prolonging the registration time by the factor N (e.g., N=20). In this case, the simultaneous registration of the object takes about as long as the sequential registration. When working with objects having fading characteristics, the advantage of the simultaneous, three-dimensional registration lies, however, in one similar (i.e., more similar) fading characteristic for all targets (of a given spectral signature) of the observation volume; this reduces shifts in the point of concentration of the fluorescence emission image caused by fading.

When working with objects having a time-dynamic structure (e.g., cells tagged in vivo), the localization accuracy of the individual object points is reduced, it is estimated, by the factor $\sqrt{N}$ (when N=20, e.g., 4.5), given a recording time (e.g. 1 second instead of 20 seconds) shortened by the factor N over the sequential registration. For example, at a three-dimensional localization accuracy in the wave field microscope of approx. ±3 nm, obtained with sequential recording times of 1 second per image plane, under the mentioned conditions, with simultaneous registration (1 second), localization accuracy is reduced, it is estimated, to ±4.5·3 nm≈14 nm, with 20 object planes being simultaneously recorded under otherwise the same conditions. However, given an assumed object movement (average shift) of 5 nm/second (as an example), the actual localization inaccuracy obtained during a sequential recording with a total registration time of 20 seconds, would be considerably greater, even without allowing for fading effects. In accordance with the present invention, object planes are simultaneously registered, as described in this case, not only with respect to an optical axis, but also with respect to two and three orthogonal optical axes.

If needed, this simultaneous image recording in accordance with the present invention can be easily combined with a conventional, sequential image recording.

Example 4

DNA Sequencing Using Multi-Dimensional Wave Field Microscopy

Known methods, such as polymerase chain reaction, are used to produce all complementary subsequences of the DNA sequence to be analyzed. The subsequences all begin at the same nucleotide of the sequence to be analyzed. The fragments to be analyzed are all tagged at the 3' end with a reference fluorochrome label $\alpha$. At the other end, the 5' end, i.e., at defined intermediate locations, they are each tagged with a fluorochrome label a, g, c, t of different spectral signatures, depending on whether the nucleotide has the base adenine (label a), guanine (label g), cytosine (label c) or thymine (label t).

All types of the fluorochrome labels used are distinguished by their spectral signatures such that the fluorochrome labels $\alpha$, a, g, c, t (in some instance, others as well) can be detected separately from one another: a specific fluorochrome label can be produced in accordance with the present invention from one to a plurality of fluorochrome molecules of the same or different type, the length and composition of the fluorochrome labels being selected in accordance with the invention so as to enable distance measurements between the maxima of the intensity distributions from beginning fluorescence labels $\alpha$ and terminal fluorescence labels (either a, or g, or c, or t, or in some instances others, for other bases) using the method of multi-dimensional wave field microscopy, i.e., in this context, linker molecules for fluorescence labels must, for example, be shorter than ½ the nucleotide diameter. In accordance with the present invention, longer linker molecules can be used, provided that they their configuration is rigid enough to ensure that they cause minimal distance variation, for example <½ nucleotide diameter.

The subsequences labeled in this manner completely represent the DNA sequence to be analyzed. The fluorescence labels a, g, c, t, i.e., the reference fluorochrome $\alpha$, can each contain one or more fluorochrome molecules. Thus, the DNA subsequences are all fixed to suitable carriers, so that they are all present as a linear sequence.

The fluorochrome-labeled DNA segments are linearly aligned using DNA combing techniques. In contrast to the typical "one-dimensional" wave field microscope, the multi-dimensional wave field microscope of the present invention eliminates the need for an additional precise alignment of the DNA strands in the direction of the system's optical axis. The DNA sequences are preferably placed on a rectangular glass fiber, whose refractive index differs minimally from that of the surrounding medium, the alignment being carried out at a specific angle, in particular orthogonally to the axis of the glass fibers, and the average distance of the maxima of the DNA sequences from one another being greater than the width at half maximum intensity of the point spread function used to register the fluorescence signals. Another method binds the 3' end to a micro-spherule of the spectral signature $\alpha$ and subsequently stretches the DNA thread using the optical tweezers tool, it being necessary to select the appropriate "tweezers laser" with respect to its wavelength.

Once the DNA sequences have been linearized, i.e., oriented, the thus produced specimen is fixed, and the molecular movement reduced, e.g., by lowering the temperature. Alternatively, the DNA ends can also be embedded in a crystalline-ordered solid structure. For calibration purposes when performing the measurement, in particular polychromatic micro-objects are introduced to the glass fiber, the DNA slide, or into the fixing solid of the DNA ends. In addition, the calibration objects contain a spectral signature, which is not a, t, c or g.

There is no need for linearization of the DNA strands when all nucleotides have been suitably fluorescence-labeled during synthesis of the DNA complementary strand to be analyzed.

The fixed DNA sequences are introduced into a multi-dimensional wave field microscope, the linear DNA subsequences being so oriented to the standing wave fronts that an exact distance measurement (accuracy $\leq 1 \cdot 10^{-10}$ m) between $\alpha$ and a, i.e., g, c or t—is possible, once the intensity bary centers are determined and the imaging properties are calibrated.

The measurement is accompanied by in situ calibration, using the calibration method of the present invention. The signals of the fluorochrome labels are registered, as spectrally separated signals, (preferably digitally) in the wave field microscope using properly adapted increments. The DNA base sequence of the DNA segment to be analyzed can be determined from the distances of the fluorescence labels and their spectral signature.

Instead of or in addition to a spectral separation, fluorescence lifetime parameters can also be analyzed. In a first phase of the evaluation, the points of concentration of the flourochrome-label signals are roughly determined, and on the basis of this information, the signals belonging to a DNA sequence are separated, in accordance with the above named distance criteria, from the other signals belonging to another DNA sequence; in a second phase of the evaluation, the spectrally separately registered, modulated signals of the fluorochrome labels are analyzed with the assistance of suitably adapted functions; from this, the distances of, e.g., the points of concentration of the beginning and terminal fluorochrome label signals of a DNA sequence, from one another, are determined with molecular precision, taking into consideration the measurements made at the calibration objects to correct distance aberrations, e.g., chromatic shifts; in a third phase of the evaluation, the distances of the fluorochrome label signals corresponding to the lengths of the DNA sequences are ordered according to increasing length, separately according to the type of terminal fluorochrome label (e.g., a, g, c, t); the arrangement thus attained corresponds to the pattern achieved using a conventional method, from which the desired sequence information can then be extracted using known methods.

One proceeds analogously in the case of macromolecules in a linear sequence or in a known ordered structure, the number and type of fluorochrome labels depending on the number and type of molecular units.

In the case that the measurement of individual DNA strands necessitates aligning them in the direction of the optical axis, then one can proceed in accordance with the present invention as follows: in addition to tagging the known end of the DNA chain with a fluorescence label of the spectral signature a, it is also tagged with a chemical "label". The rest of the DNA chain preparation, in particular the tagging of the terminal fluorescence labels a, c, g and t (stop nucleotides), is carried out, as described at the outset. The terminal bases and/or the labels of the stop nucleotides, and, in some instances, other bases of the DNA chains to be aligned, carry an electrical charge (e.g., negative).

The alignment of the DNA chains can take place before or during the microscopy; the alignment process prior to the microscopy will be described here first.

The prepared DNA chains are applied in solution, in a buffer of low ionic strength, to a specially coated slide (or cover slip, also referred to in the following as slide), which can bind ("attach to") the chemically labeled 3' end of each DNA chain. Added to the solution at this point is an immobilizing component, which, after a certain time, effects a hardening of the DNA chains in solution. The slide is covered by an (uncoated) cover slip, and is sealed, with the distance from the slide to the cover slip being adjustable by a suitable "spacer" (e.g., a thin membrane) to a well defined value. The thus sealed slide is exposed to an appropriately homogeneous, static, electrical field, which aligns the electrically charged bases. In so doing, the electrical field (for example of the one capacitor) must be polarized in such a way that, in the case of negatively (positively) charged bases, the cathode (anode) is situated near the coated slide (with the "attached" 3' ends), and the anode (cathode) near the uncoated cover slip. The electric lines of force run normal to the slide surface, and the electrical field strength is selected to be great enough to effect an alignment of the DNA chains in the solution. Once the thus aligned DNA chains are immobilized in the interstitial space of the slide—cover slip, they are recorded, i.e., measured using the multi-dimensional wave field microscope, as described above.

If the DNA chains are to be oriented during the microscopic observation, the above described electrical field is established in accordance with the present invention using the following methods:

The coated slide is an electrically conductive reflector of sufficient planeness. The solution of the DNA chains (low ionic strength) is suitably viscous, and no immobilizing components are added to the solution. Here as well, a cover slip is applied (if indicated, with the use of a suitable spacer), and sealed. At this point, the wave field is produced using only one objective lens, in conjunction with the reflector, with the excitation light emerging from the objective lens being reflected by the reflector and forming a one-dimensional wave field (in parallel to the focal plane or the reflector surface). The application of a positive (negative) voltage accompanied by the use of negatively (positively) charged bases likewise effects an alignment of the DNA chains normal to the reflector surface, thus along the optical axis of the microscope, permitting them to now be sequenced in the above described manner. Also, in applying this method, the strength of the electrical field must be great enough to effect the alignment of the DNA chains; thermal movements of the molecules can be reduced, for example, by lowering the temperature.

One can proceed analogously to this example, using any other linearized macromolecules.

Example 5

Multi-Dimensional Type II Wave Field Microscope Having Laterally, Spatially Modulated Flourescence Excitation The multi-dimensional wave field microscope type II includes, in the spatial directions x, a real illumination source for light beams, capable of coherence, a beam splitter for decoupling beam components, as a virtual illumination source, and a first objective lens, allocated to these two illumination sources. Into this first objective lens are launched the light beams, i.e., light wave trains of the illumination sources in such a way that they produce, i.e., exhibit spaced apart focal points on the focal plane (this plane is also referred to as "back focal plane") facing away from the object space, and run in the space between the two focal planes at a specific angle to one another and interfere to form a one-dimensional, standing wave field:

If one focuses a light beam (light wave train), at an appropriate distance to the optical axis, into this focal plane, (the optical axis is normal to the focal plane and runs through its center point), then, in the object space, a parallel light bundle having plane wave fronts exits the objective lens and, in fact, at a defined angle to the optical axis. This angle is variably adjustable, depending on the angle to the optical axis at which the light beams are injected into the objective lens and also depending on which type of objective lens it is.

If one injects the second light beam (light wave train) into the same objective lens, at such an angle to the first light beam and to the optical axis that its focal point lies on the rear focal plane, diametrically opposite the focal point of the first light beam, so that focal point 1—optical axis—focal point 2, therefore, form a line on the rear focal plane, then in the space between the two focal planes, a second parallel light bundle having plane wave fronts is formed, which runs at a defined angle to the first and interferes with this first light beam in the object space to form a one-dimensional, standing wave field with streaks of maximal light intensity.

Mounted in a mirror-inverted arrangement at a distance from the first objective lens is a second objective lens, so that these two objective lenses are disposed on two opposing sides of the three-dimensional object space. A third and a fourth (real or virtual) illumination source for light beams, capable of coherence, are allocated to this second objective lens in such a way that one can focus the light beams of both illumination sources—as described for the first objective lens—onto the rear focal plane of this second objective lens, i.e., the focal plane facing away from the object space, in the space between the two focal planes of this second objective lens, and allow them to interfere in the space between the two focal planes of this second objective lens to form a one-dimensional, standing wave field, and to be forced into interference in the object space, with the one-dimensional standing wave field of the first objective lens, so as to form a three-dimensional wave field having points of maximal intensity, which continue in the three-dimensional space.

To produce a two-dimensional wave field (i.e., points of maximal intensity in a plane), the described set-up is modified to the extent that one uses either a first and a second objective lens, but only combines one of these with an illumination source, or one employs only one single objective lens, and combines it with a third illumination source, whose light beams, capable of coherence, one injects in such a way with respect to the light beams of the two other illumination sources, into this single objective lens that the corresponding three focal points form, on the focal plane, an equal-sided triangle, through whose midpoint, the optical axis runs. In the object space, all three light beams exit the microscope objective at the same angle to the optical axis, but each in a different direction.

This variant of the wave field microscope type II according to the present invention for producing a multi-dimensional wave field microscope using a single objective lens can also be used to generate a three-dimensional wave field. For this, one directs four light beams into the same objective lens and, in fact, in such a way that the four focal points corresponding thereto form an equal-sided square in the rear focal plane.

What is claimed is:

1. A wave field microscope comprising:
    an illumination system for illuminating an object for examination with a plurality of coherent light beams through at least one objective lens arrangement, the object having a plurality of object structures, the light beams interfering in at least one object plane and illuminating the object in the object plane with an interference pattern;
    an optical detection system; and
    a holding device for the object,
    the interference pattern being a two- or three dimensional point pattern generated by two or three standing wave fields,
    the object being shiftable relative to the point pattern, each object structure causing a modulation of the light detected by the optical detection system within a detection point spread function, the modulation being given by the point spread function of the wave field microscope through convolution of the point pattern and the detection point spread function,
    for each object structure, a maximum of the point spread function of the wave field microscope being detectable within the detection point spread function using intensity measurements,
    a space between two object structures being detectable as a function of values of the maximums of the point spread function of the wave field microscope for the two object structures so as to permit the wave field microscope to measure geometric distances between the object structures.

2. The wave field microscope as recited in claim 1 wherein the optical detection system detects fluorescent light.

3. The wave field microscope as recited in claim 1 wherein the interfering light beams are adjustable to be aligned antiparallel or at a variable angle to one another.

4. The wave field microscope as recited in claim 1 wherein the lens arrangement has at least two spatial directions, the lens arrangement having in at least one of the spatial directions a first objective lens with a first numerical aperture or a first reflector assigned to a second objective lens with a second numerical aperture higher than the first numerical aperture, and, in at least one of the other spatial directions, the lens arrangement has two other objective lenses with other numerical apertures lower than the second numerical aperture, or a third objective lens with a third numerical aperture lower than the second numerical aperture and a second reflector assigned to the third objective lens.

5. The wave field microscope as recited in claim 1 wherein the illumination system includes at least one first illumination source for the light beams capable of coherence and at least one beam splitter for decoupling at least one of the light beams, the lens arrangement including a common lens assigned to both the first illumination source and the at least one beam splitter, the light beams and beam splitter capable of being coupled to said common lens so that on a rear focal plane facing away from an object space, the light beams produce two spaced apart focal points, and that in a further space between the rear focal plane and a further focal plane in the object space the light beams run in a variably-adjustable angle to one another and interfere to create a standing wave field.

6. The wave field microscope as recited in claim 5 wherein the illumination system further comprises at least one additional coherent light beam, and the lens arrangement includes a further objective lens being assigned to additional coherent light beam, the further objective lens capable of directing and aligning the additional coherent light beam in the object space so that the additional coherent light beam interferes with the standing wave field produced by the light beams so as to generate the point pattern.

7. The wave field microscope as recited in claim 1 wherein the detection system comprises at least one detection objective lens.

8. The wave field microscope as recited in claim 1 wherein the holding device is arranged in the wave fields and is capable of being rotationally mounted about an axis.

9. The wave field microscope as recited in claim 8 wherein the holding device is capable of being rotated 360 degrees about the axis.

10. The wave field microscope as recited in claim 1 point pattern is capable of being rotated about an axis.

11. The wave field microscope as recited in claim 1 wherein the holding device or the point-pattern are capable of being rotated about an axis so as to illuminate the object sequentially or simultaneously with the point pattern.

12. The wave field microscope as recited in claim 1 wherein the detection system includes a scanner reflector arranged so as to be suitable for forming an image of the object structures using the intensity measurements.

13. The wave field microscope as recited in claim 1 wherein the illumination system includes in at least one first spatial direction a real illumination source for two- or multi-photon excitation, and in at least one other spatial direction, another illumination source for the two- or multi-photon excitation, and the standing wave fields ($WF_1$, $WF_2$, ..., $WF_i$) generated having wavelengths ($\lambda_1, \lambda_2 ..., \lambda_i$) differing from one another, and having distances ($d_1, d_2, ..., d_i$) between specific wave maxima or wave minima of $d_1=\lambda_1/2n \cos \theta_1$ or $d_2=\lambda_2/2n \cos \theta_2$ or $d_i=\lambda_i/2n \cos \theta_i$ where n equals the index of refraction in an object space and $\theta_1, \theta_2, \ldots \theta_i$ equals an intersection angle of the light waves of the wavelengths $\lambda_1, \lambda_2 \ldots, \lambda_i$ with an optical axis, and with the wave fields $WF_1$, $WF_2 \ldots W_i$ being aligned with respect to one another so that at least a maximum of at least two standing wave fields is situated at a same place.

14. The wave field microscope as recited in claim 1 wherein the lens arrangement has at least two spatial directions, the lens arrangement having in at least one of the spatial directions a first objective lens with a first numerical aperture, and, in at least one of the other spatial directions, the lens arrangement has an other objective lenses with an other numerical aperture lower than the first numerical aperture.

* * * * *

UNITED STATES PATENT AND TRADEMARK OFFICE
CERTIFICATE OF CORRECTION

PATENT NO. : 7,342,717 B1
APPLICATION NO. : 09/462435
DATED : March 11, 2008
INVENTOR(S) : Michael Hausmann et al.

It is certified that error appears in the above-identified patent and that said Letters Patent is hereby corrected as shown below:

On the Title Page, Item (73) Assignee should read:

--Ruprecht Karls Universitaet Heidelberg, Heidelberg (DE)-- instead of

"Ruprecht Karts Universitaet Heidelberg, Heidelberg (DE)"

Column 1, line 36 should read:

--...are bound to specific (sub)structures in biological micro-...-- instead of

"...are bound to specific (substructures in biological micro-..."

Column 5, line 9 equation should read:

$$--D^2_{kB} = (x_B - x_k)^2 + (y_B - y_k)^2 + (z_B - z_k)^2--$$

instead of $$"D^2_{kB} = (z_B - x_k)^2 + (y_B - y_k)^2 + (z_B - z_k)^2"$$

Signed and Sealed this

Fifth Day of August, 2008

JON W. DUDAS
*Director of the United States Patent and Trademark Office*